United States Patent
Krätschmer et al.

(10) Patent No.: US 10,094,775 B2
(45) Date of Patent: Oct. 9, 2018

(54) SENSOR ARRANGEMENT FOR DETERMINING TURBIDITY

(71) Applicant: Endress+Hauser Conducta GmbH+Co. KG, Gerlingen (DE)

(72) Inventors: Thilo Krätschmer, Gerlingen (DE); Ralf Bernhard, Stuttgart (DE); Matthias Grossmann, Vaihingen-Enz (DE); Benjamin Bertsch, Gerlingen (DE)

(73) Assignee: ENDRESS+HAUSER CONDUCTA GMBH+CO. KG, Gerlingen (DE)

(*) Notice: Subject to any disclaimer, the term of this patent is extended or adjusted under 35 U.S.C. 154(b) by 0 days.

(21) Appl. No.: 15/372,491

(22) Filed: Dec. 8, 2016

(65) Prior Publication Data
US 2017/0160194 A1   Jun. 8, 2017

(30) Foreign Application Priority Data

Dec. 8, 2015   (DE) .................... 10 2015 121 358

(51) Int. Cl.
*G01N 21/00*   (2006.01)
*G01N 21/51*   (2006.01)
(Continued)

(52) U.S. Cl.
CPC ............. *G01N 21/51* (2013.01); *G01N 21/53* (2013.01); *G01N 21/8507* (2013.01);
(Continued)

(58) Field of Classification Search
CPC .............. G01N 21/53; G01N 21/538; G01N 2021/4709; G01N 15/0205; G01N 21/21
(Continued)

(56) References Cited

U.S. PATENT DOCUMENTS 6,864,985 B1    3/2005   Tanzer
7,659,980 B1 *  2/2010   Mitchell ............ G01N 21/4785
                                                      356/338

(Continued)

FOREIGN PATENT DOCUMENTS

DE    19714695 A1    10/1998

OTHER PUBLICATIONS

Search Report for German Patent Application No. 10 2015 121 358.3, German Patent Office, dated Sep. 26, 2016, 6 pp.

*Primary Examiner* — Md M Rahman
(74) *Attorney, Agent, or Firm* — Christopher R. Powers; PatServe (57) ABSTRACT

The present disclosure relates to a sensor arrangement for determining the turbidity of a liquid medium. The sensor arrangement includes a sensor section with at least one light source for sending transmission light into a measuring chamber, and at least one receiver associated with the light source for receiving reception light from the measuring chamber, wherein the transmission light is converted into the reception light in the measuring chamber by the medium by means of scattering at a measurement angle, and the reception light received by the receiver is a measure of the turbidity. The reception light is back reflected at a reflection element in contact with the medium, whereby an optical path from the light source through the measuring chamber to the reflection element and from the reflection element through the measuring chamber to the receiver results.

18 Claims, 7 Drawing Sheets

(51) Int. Cl.
*G01N 21/53* (2006.01)
*G01N 21/85* (2006.01)
*G01N 21/47* (2006.01)

(52) U.S. Cl.
CPC ............... *G01N 2021/4709* (2013.01); *G01N 2021/4711* (2013.01); *G01N 2021/4728* (2013.01); *G01N 2021/513* (2013.01); *G01N 2021/8521* (2013.01)

(58) Field of Classification Search
USPC ........................................................ 356/342
See application file for complete search history.

(56) References Cited

U.S. PATENT DOCUMENTS

| | | | | |
|---|---|---|---|---|
| 2006/0061765 | A1* | 3/2006 | Rezvani | G01N 21/49 356/442 |
| 2007/0046525 | A1* | 3/2007 | Holbrook | G01S 13/89 342/22 |
| 2007/0046942 | A1 | 3/2007 | Ng et al. | |
| 2007/0222986 | A1* | 9/2007 | Palumbo | G01N 15/0227 356/338 |
| 2014/0312212 | A1* | 10/2014 | Schappacher | G01J 3/26 250/225 |

* cited by examiner

PRIOR ART

SENSOR ARRANGEMENT FOR DETERMINING TURBIDITY

CROSS-REFERENCE TO RELATED APPLICATION

The present application is related to and claims the priority benefit of German Patent Application No. 10 2015 121 358.3, filed on Dec. 8, 2015, the entire contents of which are incorporated herein by reference.

TECHNICAL FIELD

The present disclosure relates to sensors, in particular a sensor arrangement for determining the turbidity of a liquid medium.

BACKGROUND

Any light striking particles suspended in a liquid is scattered. The intensity of this light scattering is used in optical turbidity measurement as a direct measure for the determination of turbidity. Different measurement angles are used for different applications—in part due to national and local legal provisions and regulations. For example, 90° scattered light is used in drinking water applications, among others. Breweries often use a scattered light angle in the range of 11° to 25°. In measurements in sludges, a back-scattering angle of >90° (e.g., 135°) is commonly used. "FNU" units (Formazin Nephelometric Units) are often used as reference measurement or for turbidity values.

Figure 1:
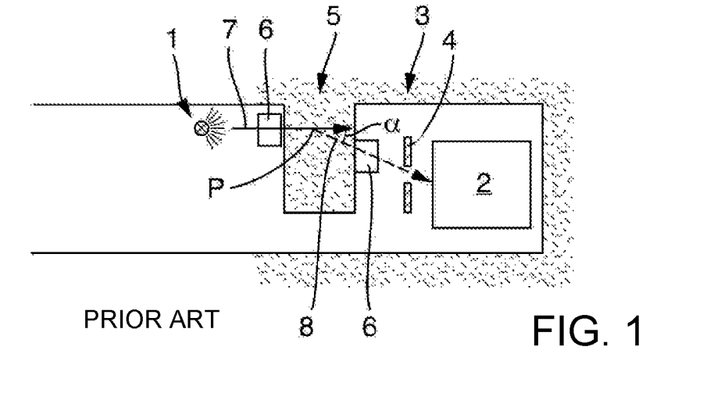
FIG. 1 shows a conventional turbidity sensor arrangement according to the prior art.

Typically, a turbidity sensor based upon scattered light measurement can be illustrated as in FIG. 1. From the light source 1, transmission light 7 (solid line) is radiated through a window 6 that is transparent to the transmission light 7 into a measuring chamber 5. There, the light is scattered on particles in the medium 3 at a scattering point P at a measurement angle α or converted into reception light 8 (dashed line). Through a window 6 that is transparent to the reception light 8, the reception light arrives at a receiver 2 through, for example, an aperture 4. The light intensity arriving at the receiver 2 is a measure of the turbidity.

However, problems can occur in this process. Due to the optical windows 6 on both sides of the measuring chamber 5 and due to the active elements likewise on both sides of the measuring chamber 5 (such as electronic components, light source, receiver), the assembly of the turbidity sensor is complex and cost-intensive.

If several scattered light angles are to be measured using a single sensor, i.e., for example, 11° and 25°, or 90° and 180° and 11°, the problems described above are further exacerbated.

SUMMARY

The present disclosure is based upon the aim of suggesting a sensitive and flexible turbidity sensor that is easy to manufacture.

The aim is achieved by a sensor arrangement comprising: a sensor section with at least one light source for transmitting transmission light into a measuring chamber containing a medium, and at least one receiver associated with the light source for receiving reception light from the measuring chamber, wherein the transmission light in the measuring chamber is converted by the medium into the reception light by means of scattering at a measurement angle, and the reception light received by the receiver is a measure of the turbidity. The arrangement is characterized in that reception light is back reflected at a reflection element, wherein the reflection element is in contact with the medium, whereby an optical path from the light source via the measuring chamber to the reflection element and from the reflection element via the measuring chamber to the receiver results.

In a further development, transmission light is additionally back reflected at the reflection element, whereby an optical path from the light source via the measuring chamber to the reflection element and from the reflection element via the measuring chamber to the receiver results.

In the medium, the transmission light coming from the light source is scattered by particles at different scattering points at all solid angles. The distribution of the scattering intensity to the different solid angles is, in the process, dependent upon the particles. This scattered light is again deflected by the reflection element toward the light source or toward the receiver. In the process, the angle is preserved due to the law of reflection (angle of incidence equals angle of reflection). This preservation of the angle is decisive, since the reflected transmission light also strikes particles and is there scattered at additional scattering points. As a result of the preservation of the angle, all scattered light rays that were scattered at the same measurement angle run parallel.

Two possible paths starting from the light source can thus be distinguished. In one, light is first scattered, and then reflected. In the other, light is first reflected, and then scattered.

In the case last mentioned, situation 1 (i.e., "back reflection and light scattering at the measurement angle α") and situation 2 (i.e., "light scattering of the incident transmission light at the associated supplementary angle δ") generally cannot be distinguished. In this case, the supplementary angle is defined as 180° minus the measurement angle (δ=180°−α). In one embodiment, scattered light that is generated after the back reflection of the incident transmission light is not directed onto the detector.

The frequent case of the 90° scattered light measurement, i.e., measurement angle α=90°, is to be highlighted here. In this case, the limitation does not occur, since 90°=180°−90°. The light yield at the receiver can thereby be improved according to the present disclosure, since the light that is scattered at the scattering point arrives twice at the receiver (once from the incident light and once from the back-reflected light). The same applies if a general scattering angle and the associated supplementary angle do not have to be distinguished, e.g., in scattering media that have the same emission characteristics for these two angles, or in cases where this distinction is not required. For 90° scattered light measurements and for cases where a distinction between a scattered light angle and its supplementary angle does not need to be made, a higher measurement signal results, and thus a more sensitive measurement.

Generally, the construction is more flexible, which is made clear by the embodiments described below. The sensor arrangement can be constructed in a compact and robust manner.

Naturally, both on the path to the reflection element and on the path from the reflection element, light is also scattered at other angles, i.e., not at the measurement angle. In order that this undesired light not falsify the measurement result, the sensor section comprises at least one solid angle filter that directs the light scattered and back reflected by the reflection element onto the receiver, wherein only light scattered at the measurement angle passes through the solid angle filter.

Here, in this context, the term "measurement angle" is to be understood as the measurement angle itself plus/minus a tolerance range, i.e., for example, ±10°, including ±5°. There are also applications that are possibly subject to a standard that requires certain limits. To be mentioned in this respect is, for example, the limit of ±2.5° for the angle range in drinking water (see DIN ISO 7027).

In another development, the solid angle filter comprises at least one optical beam-shaping component, for example, a lens. Reception light can thereby be directed even better toward the receiver.

In a first embodiment, the solid angle filter comprises a hollow cylinder that absorbs at least a portion of the reception light, wherein the hollow cylinder, due to its inner diameter and its length, allows only reception light to pass through that was scattered at the measurement angle. In this case, the hollow cylinder can have a circle as base, whereby the hollow cylinder is designed as a pipe. However, the base may just as well be angular, such as square, generally rectangular, or comprising any number of corners. Even though the term "inside diameter" connotes a circular base be used, in the sense of this present disclosure, "inside diameter" is to mean the minimum distance between two opposite surfaces when the base is not circular. In an embodiment with regard to the hollow cylinder, pinholes with a distance defining the measurement angle can also be seen.

In another embodiment, the solid angle filter comprises a block that absorbs at least a portion of the reception light, which block comprises several openings in the direction of the incident reception light, wherein the block, due to the number of openings, the inner diameter of the openings, and the distance of the openings from one another, allows only reception light to pass through that was scattered at the measurement angle.

In the same way, one or more glass fibers or glass fiber bundles can be arranged accordingly. Another alternative is to be seen in a film stack. Naturally, a combination of the embodiments presented is also possible.

In another, first embodiment, the reflection element is not mechanically connected to the sensor section. This first embodiment comprises at least two variants. In the first variant, the reflection element is formed by a housing section of the sensor arrangement, said housing section being associated with the sensor section and arranged, for example, on an opposite side of the container, on which the sensor arrangement is attached. In a second variant, the reflection element is formed by the container itself, such as by its wall. In a second embodiment, the sensor section comprises the reflection element. The sensor section and a reflection section comprising the reflection element are thus designed as one piece.

In an embodiment, the transmission light is scattered at a first measurement angle and at least one second measurement angle, and the sensor arrangement comprises a first solid angle filter for the first measurement angle and at least one second solid angle filter for the second measurement angle. Turbidity can thus be determined at several measurement angles using the sensor arrangement. The solid angle filters ensure that only the respectively scattered light arrives at the receiver.

In such an embodiment, the sensor arrangement comprises a first receiver for reception light scattered at the first measurement angle and a second receiver for reception light scattered at the second measurement angle. Each receiver is associated with a certain measurement angle; the light of the respective measurement angle does not need to first be filtered at each receiver. A simpler construction becomes possible.

In an embodiment, the sensor arrangement comprises a first light source for sending transmission light into the measuring chamber at a first angle of incidence and a second light source for sending transmission light into the measuring chamber at a second angle of incidence, wherein the light of the first light source is scattered at a first measurement angle, and the light of the second light source is scattered at a second measurement angle.

A combination of the two variants presented is also possible, viz., with several light sources and several receivers.

In another embodiment, the reflection element comprises a first section and at least one second section, wherein the first section reflects light at a first angle of reflection, and the second section reflects light at a second angle of reflection toward the first or second solid angle filters respectively. Only by the division into different sections is it possible with certain measurement angles to use the effect of the back reflection. In addition, a space-saving construction can be achieved.

The reflection element is arranged at an angle other than 90° relative to the transmission light. Such an embodiment increases the flexibility with respect to the measurement angles. In addition, the construction becomes simpler.

As a space-saving and cost-effective embodiment with good optical properties, the reflection element comprises a reflection prism.

In another embodiment, the sensor arrangement comprises, as a boundary between the sensor section and the measuring chamber, a first window that is transparent to the transmission light, and/or a second window, wherein the second window, as a boundary between the measuring chamber and the sensor section, is transparent to the reception light.

In an embodiment, and in order to save space, as well as to simplify manufacturing, the first and the second windows are designed as a common window.

If the optical properties of the window are to be adjusted for the respective measurement angle, the sensor arrangement alternatively and preferably comprises one window per measurement angle, and the respectively scattered reception light passes through the corresponding window.

In another embodiment, the sensor section comprises a fiber-optic cable between the solid angle filter and the receiver. This represents a simple and good option for conducting the light over longer distances, without greater losses.

BRIEF DESCRIPTION OF THE DRAWINGS

The present disclosure is explained in more detail with reference to the following figures. These show.

In the figures, the same features are marked with the same reference symbols.

DETAILED DESCRIPTION

Figure 3A:
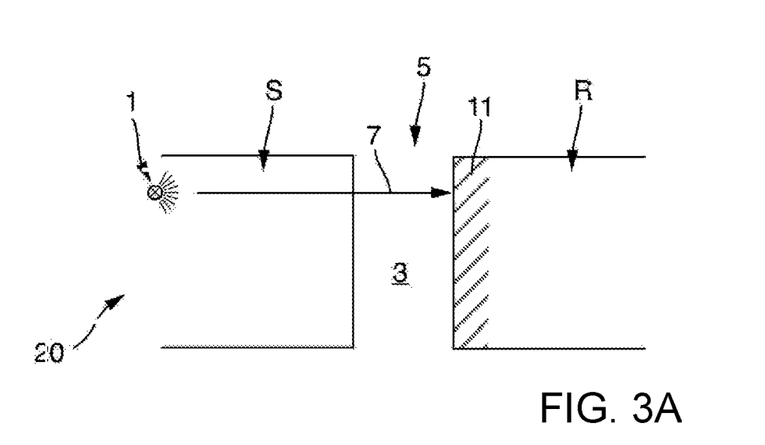
FIGS. 3A-3G show a step-by-step explanation of the principle of the sensor arrangement for determining turbidity according to the present disclosure.

The measurement method of a turbidity sensor is known and has already been explained above. The basic features are explained only briefly, although these basic features are mostly not shown in the figures. A sensor arrangement 20 according to the present disclosure, as shown in FIG. 3A, is also referred to as turbidity sensor below. The turbidity sensor is arranged on a container, for example, on a pipe. Such an embodiment may be carried out via fastening means, such as a flange. The turbidity sensor can also be arranged on an immersion or quick-change fitting or the like. The medium 3 to be measured is located in the pipe; for example, the medium 3 flows through the pipe. The medium 3 to be measured is mostly a liquid often process and waste water. The arrangement is, however, also used in fresh water, such as drinking water. The turbidity sensor is arranged substantially orthogonally to the longitudinal axis of the pipe. The turbidity sensor comprises a housing. Stainless steel, plastic, or a ceramic can be used as materials for the arrangement 20, including for the housing. As already mentioned, the turbidity sensor is often used in drinking water or waste water. The materials are selected such that they are suitable for use in, for example, waste water. The plastic must therefore be an appropriately durable plastic, such as PTFE or the like.

The arrangement 20 comprises at least one light source 1 and a receiver 2. Via electrical connections, the light source and the receiver are connected to a control unit (not shown). The control unit is, for example, a measuring transducer, control center, etc.

The receiver 2 may be designed, for example, as a photo diode, which generates a receiver signal, such as a photocurrent or a photovoltage, in response to the light received.

The light source 1, for example an LED, sends light toward the medium 3. In this respect, "light" within the meaning of the present disclosure is not to be limited to the visible range of the electromagnetic spectrum, but is to be understood as electromagnetic radiation of any wavelength, for example, also in the ultraviolet (UV) and in the infrared (IR) wavelength range. A wavelength of 860 nm may be used.

Figure 8A:
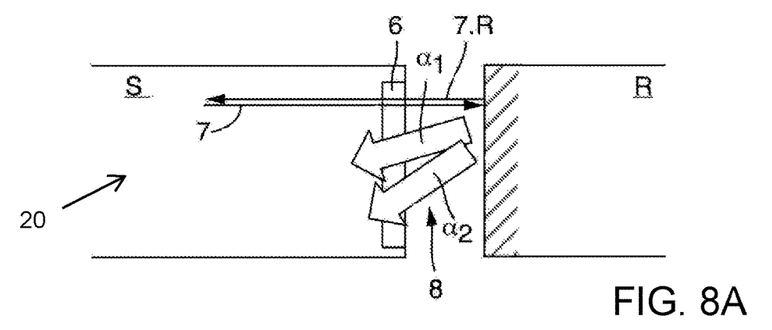
FIGS. 8A-8C show the sensor arrangement according to the present disclosure in another embodiment with respect to the windows.
Figure 8B:
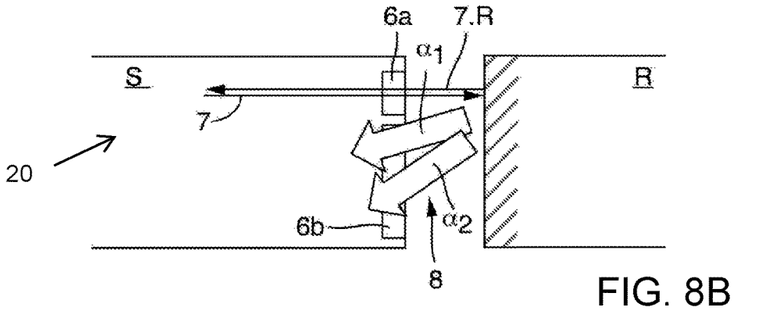
Figure 8C:
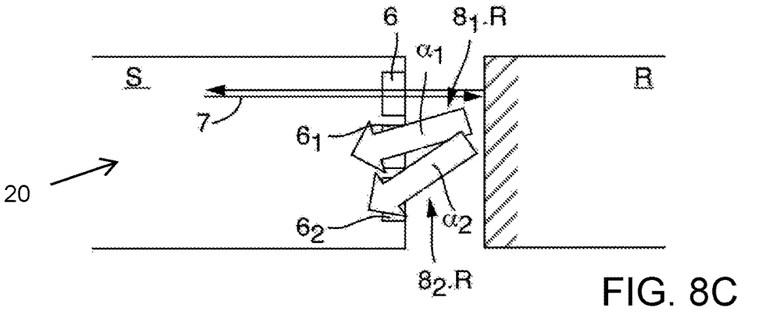

In the following, only the turbidity sensor according to the present disclosure will be discussed. FIGS. 2A-7 do not show optical windows, for the sake of clarity. Various implementation options for the optical windows are illustrated in FIG. 8 and explained below. For the same reason, the optical refraction at the transition from the window to the medium is also not illustrated or discussed. Nonetheless, the optical refraction is considered to reduce the present disclosure to practice.

The boundaries are thus through the windows (not shown) transparent to arriving light. A back-reflection plane or a reflection element 11 within the meaning of the present disclosure (details below) is illustrated in the figures as a dashed surface. Light is back reflected on these dashed surfaces. Reflected light is denoted by the suffix "R" in the reference symbols. As used herein, "back reflected" light may alternately be deflected or diffracted by the back-reflection plane or a reflection element 11.

Light already scattered is illustrated in the figures as a dashed line.

Figure 2A:
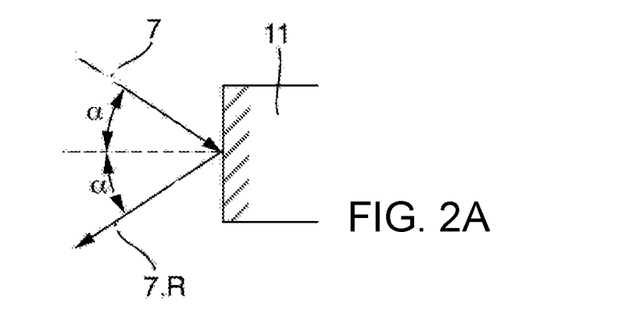
FIGS. 2A and 2B show the two basic principles of the present disclosure.
Figure 2B:
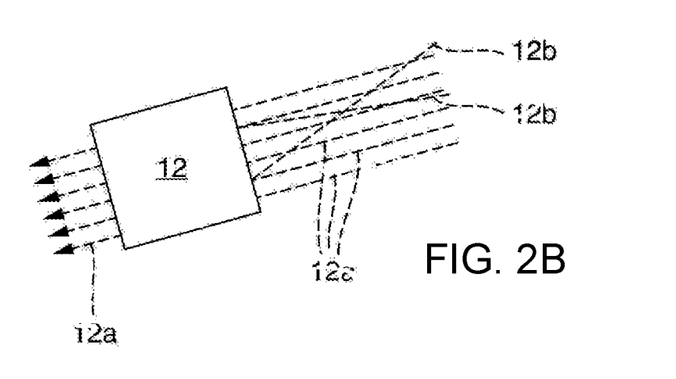

The present disclosure is based upon two principles, which are explained in FIGS. 2A and 2b: reflection and solid angle filtering. In this respect, the solid angle filtering can be considered facultative, but advantageous. The law of reflection (angle of incidence=angle of reflection) applies to at least one certain angle here, the scattered light angle α, also called measurement angle α. In a first embodiment, the reflection element is thus a mirror. A solid angle filter 12 is a passive component, in which only light with a certain angle of incidence range is allowed to pass through. Such light rays are indicated with the reference symbol 12a. Light with an angle of incidence outside the pass range is blocked by the solid angle filter, by either absorption, deflection, etc. Such light beams are marked with the reference symbol 12b. A simple solid angle filter is, for example, a black pipe that defines by its measurements with respect to inner diameter and length a certain angle range that is allowed to pass through, whereas other angles are absorbed by the material. Generally, the solid angle filter is a hollow cylinder that absorbs at least a portion of the reception light. In this case, the hollow cylinder can, as mentioned, have a circle as base, whereby the hollow cylinder is designed as a pipe. However, the base may just as well be angular, such as square, generally rectangular, or comprising any number of corners. Due to its inner diameter and its length, the hollow cylinder allows only reception light to pass through that was scattered at the measurement angle. Even though the term "inside diameter" connotes a circular base be used, in the context of the present disclosure, it is to mean the minimum distance between two opposite surfaces when the base is not circular. In an embodiment with regard to the hollow cylinder, pinholes with a distance defining the measurement angle can also be seen. Another advantageous embodiment of a solid angle filter for the present disclosure is a black, absorbing base block, in which long, thin holes are introduced at narrow distances. The block is defined by the number of openings, the inner diameter of the openings, and the distance of the openings from one another. In the same way, one or more glass fibers or glass fiber bundles can be arranged accordingly. Another alternative is to be seen in a film stack. A solid angle filter can also comprise one or more beam-shaping components, such as lenses. Naturally, a combination of the embodiments presented is also possible.

The sensor arrangement for determining turbidity according to the present disclosure, in its entirety, has the reference symbol 20. Its functionality will now be explained. The arrangement 20 comprises at least one sensor section S with the light source 1 and the light receiver 2.

First, transmission light 7 is generated using a light source 1, which transmission light may be focused and aligned by one or more optical components (apertures, lenses, etc.; not shown). This light 7 then passes through an optical window (not shown) to first arrive in a measuring chamber 5 with the medium 3 and then on a reflection element 11, here shown as a simple mirroring surface. In this regard, see FIG. 3A. The reflection element 11 is thus in contact with the medium 3. A reflection section R comprises the reflection element 11. In a first embodiment, the reflection section R is not mechanically connected to the sensor section S. This first embodiment comprises at least two variants. In the first variant, the reflection section R with the reflection element 11 is formed by a second housing section of the sensor arrangement 20, said housing section being associated with the sensor section S and arranged, for example, on the opposite side of the container. In a second variant, the reflection section R with the reflection element 11 is formed by the container itself by its wall, for example.

Figure 3B:
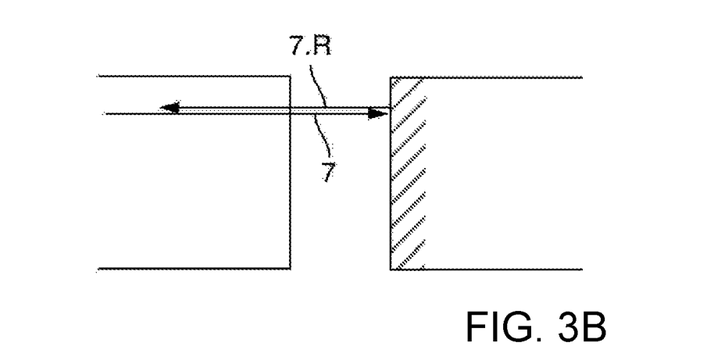

In the next step, the transmission light 7 is reflected at the same angle as it arrives; see FIG. 3B (or FIG. 2B) with the reflected transmission light 7.R.

Figure 3C:
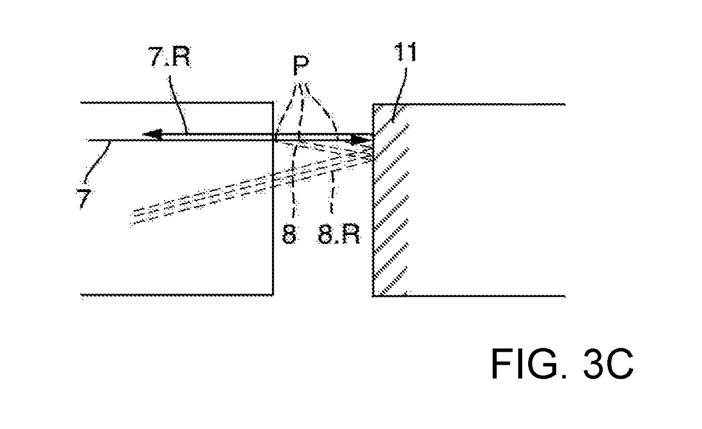

In the medium 3, the transmission light 7 coming from the light source 1 is scattered by particles at different scattering points P at all solid angles. The distribution of the scattering intensity to the different solid angles is, in the process, dependent upon the particles. In FIG. 3C, only the scattered light that is scattered at the measurement angle, i.e., for example, $\alpha=25°$, is indicated. This scattered light is again deflected by the reflection element 11 toward the light source 1 or toward the receiver 2. In the process, the angle is preserved (law of reflection), i.e., the angle of incidence equals the angle of reflection. By the scattering, the transmission light 7 is converted into reception light 8. The converted light is referred to as reception light 8 in the present disclosure. The reception light reflected by the reflection element 11 is marked with the reference symbol 8.R. Light already scattered is shown with dashed lines.

Figure 3D:
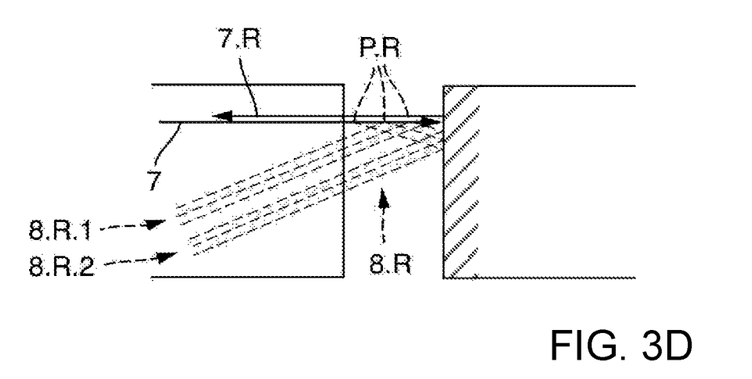

As explained above, this preservation of the angle is decisive, since the reflected transmission light 7.R also strikes particles and is there scattered at additional scattering points P.R, as shown in FIG. 3D. As a result of the preservation of the angle, all scattered light rays that were scattered at the same angle $\alpha$ run parallel. As above, light already scattered is here also shown dashed. In FIG. 3D, the upper three beams, marked with reference symbol 8.R1, are formed by reflected transmission light 7.R. On the other hand, the lower three beams, marked with reference symbol 8.R2, are first scattered, and then reflected. In both cases, parallel reception light 8.R is formed.

Figure 3E:
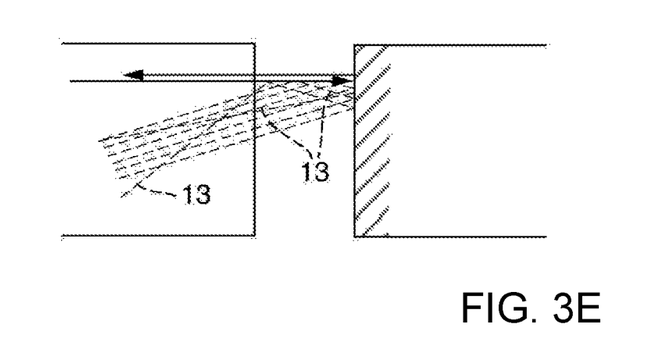

Naturally, both on the path to the reflection element 11 and on the path from the reflection element 11, light is scattered at other angles, i.e., not at the measurement angle $\alpha$. These light rays are marked with reference symbol 13, in this regard, as shown in FIG. 3E.

Figure 3F:
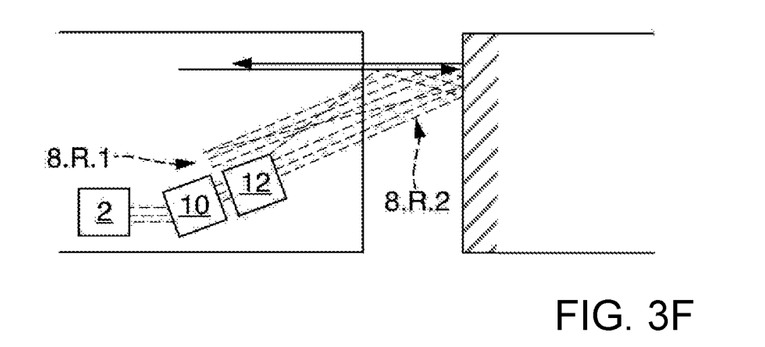

As shown in FIG. 3F, the rays that were scattered at an angle other than the measurement angle $\alpha$ are now extinguished by the solid angle filter 12, whereas all rays that were scattered at the measurement angle $\alpha$ pass through the solid angle filter 12. Then, these rays arrive, possibly by means of a fiber-optic cable 10, at the receiver 2, where they are converted into a corresponding measurement signal, from which the turbidity value is calculated.

As mentioned, two possible paths starting from the light source 1 can be distinguished. In one, light is first scattered, then back reflected (reference symbol 8.R2). In the other, light is first back reflected and then scattered (reference symbol 8.R1). In the case mentioned last, a distinction cannot be made between "back reflection and light scattering at the measurement angle $\alpha$" and "light scattering of the incident transmission light 7 at the associated supplementary angle $\delta$." The supplementary angle $\delta$ is defined as 180° less the measurement angle $\alpha$.

FIG. 3F shows an arrangement in which the transmission light scattered after the back reflection (i.e. 8.R1) is not directed onto the detector. On the other hand, FIG. 3G shows an arrangement that directs both types 8.R1 and 8.R2 onto the receiver.

The frequent case of the 90° scattered light measurement, i.e. $\alpha=90°$, is to be mentioned again with reference to FIG. 5B. The limitation mentioned above does not occur in this case, since $\delta=\alpha=90°$. The light yield at the receiver is improved, since the light that is scattered at the scattering point arrives twice at the receiver (once from the incident light and once from the back-reflected light). The same applies if a general scattering angle and the associated supplementary angle do not have to be distinguished, e.g., in scattering media that have the same emission characteristics for these two angles, or in cases where this distinction is not required. For 90° scattered light measurements and for cases where a distinction between a scattered light angle and its supplementary angle does not need to be made, a higher measurement signal results, and thus a more sensitive measurement.

In the process, the solid angle filter 12 used filters, not precisely the measurement angle $\alpha$, but light that arrives within a tolerance range, i.e., for example, within ±10, including ±5°, or including ±2.5°.

Figures 3G, 4:
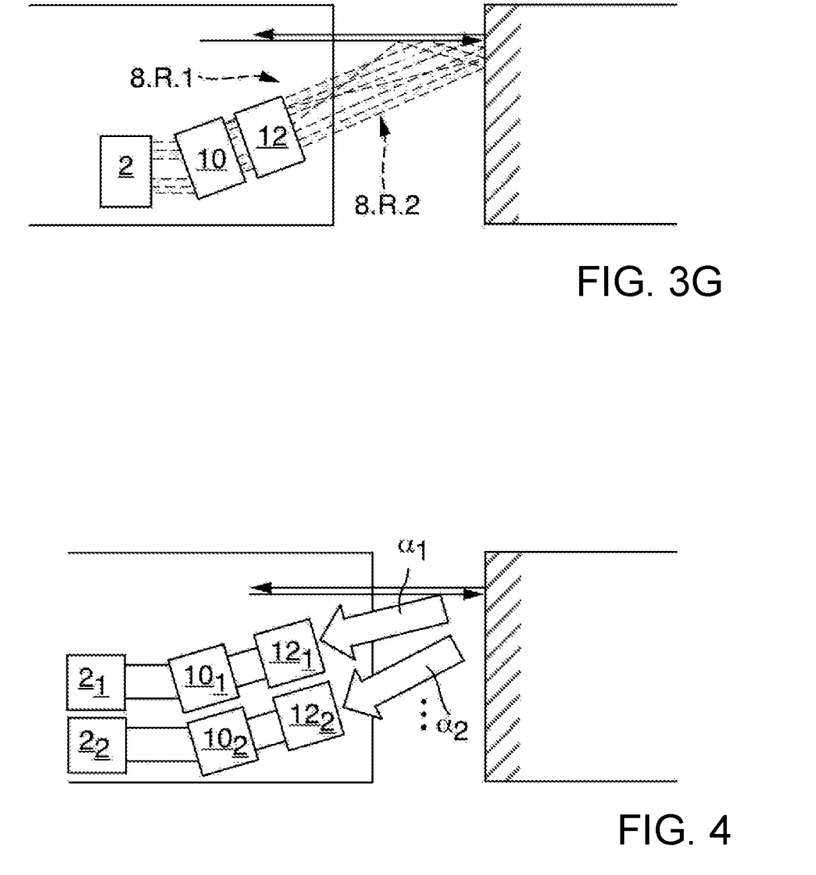
FIG. 4 shows the sensor arrangement according to the present disclosure in an embodiment with respect to several measurement angles.

In another embodiment, as shown in FIG. 4, the sensor arrangement 20 can determine turbidity not just at a single measurement angle, but also at several measurement angles $\alpha_1$, $\alpha_2$. In the following, this is explained using two different measurement angles, but additional measurement angles can, naturally, also be used. For this purpose, the sensor arrangement 20 respectively comprises, for each measurement angle $\alpha_1$, $\alpha_2$, a solid angle filter $12_1$, $12_2$. Each measurement angle $\alpha_1$, $\alpha_2$ is then associated with its own receiver $2_1$, $2_2$.

The distribution of the measurement of different angles to a light source 1 and several receivers $2_1$, $2_2$ can also be reversed, so that light from several light sources $1_1$, $1_2$ is sent exclusively at different angles $\alpha_1$, $\alpha_2$ and received by a single receiver 2 (not shown). A combination of the two possibilities is also conceivable, wherein several light sources $1_1$, $1_2$ and several receivers $2_1$, $2_2$ are used.

Figure 5A:
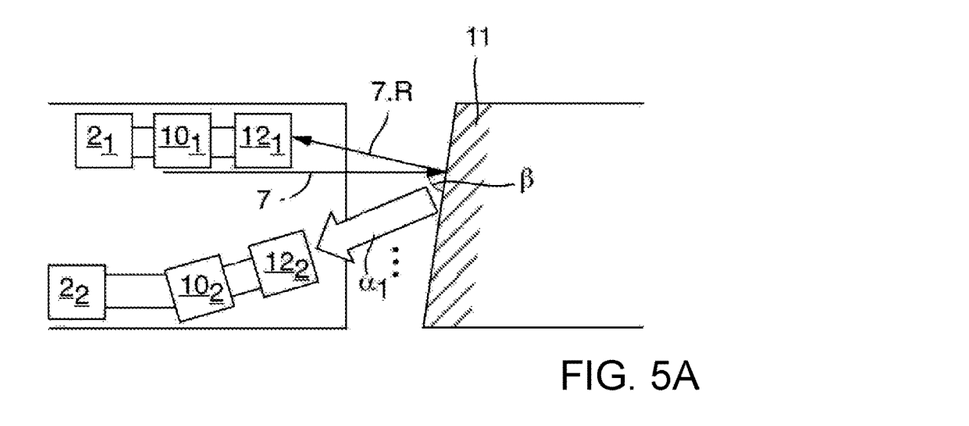
FIGS. 5A and 5B show the sensor arrangement according to the present disclosure in two additional embodiments with respect to the reflection section.
Figure 5B:
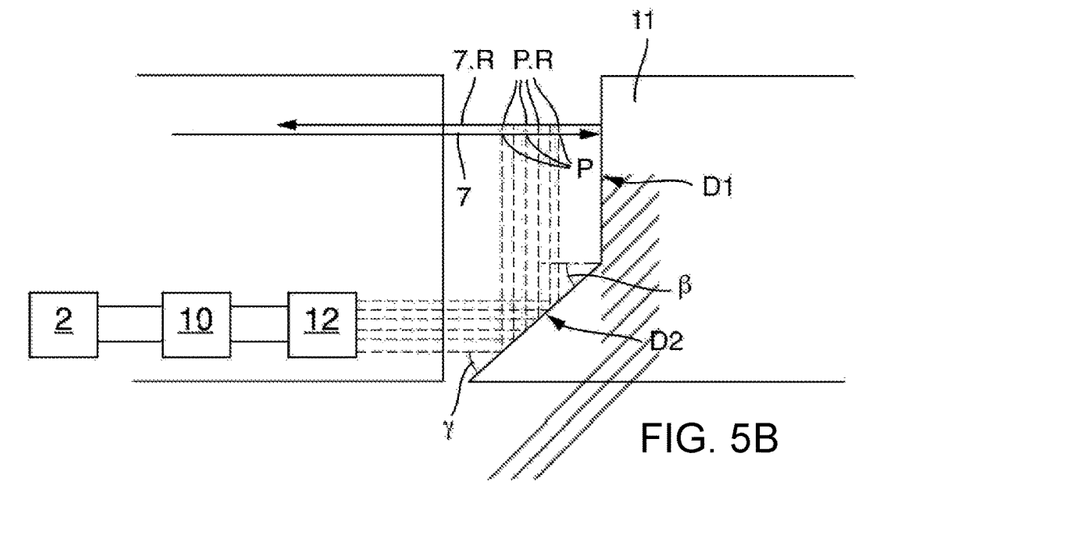

FIGS. 5A and 5B show that the reflection element 11 does not necessarily need to be aligned in parallel to the optical window. It can be advantageous for some applications to deviate from the parallelism. In other words, the reflection element 11 is arranged at an angle $\beta$ other than 90° relative to the transmission light 7.

FIG. 5A shows an angle $\beta<90°$. In this case, in contrast to the previous figures, the transmission light 7 is not directly back reflected again, but, as reflected light 7.R, is scattered at an angle or arrives then at the solid angle filter 12 at an angle.

In FIG. 5B, the reflection element 11 is divided into different sections $D_1$ and $D_2$. The arriving light is back reflected on these sections $D_1$, $D_2$ at an angle of reflection $\gamma$. An angle of reflection of about $\gamma=90°$ is shown. Only by the division into different sections is it possible with certain measurement angles $\alpha$ to use the effect of the back reflection. In the example, light at a measurement angle of $\alpha=90°$ can first be back reflected by section $D_2$, which is arranged at an angle $\beta=45°$.

As explained in the previous examples and above, the reflection element 11 in the reflection section R can be arranged to be offset from the sensor section S. The reflection section R and the sensor section S can, however, also be designed as one piece. In other words, the sensor arrangement 20 then comprises the sensor section S and the reflection section R. These embodiments are shown in FIGS. 6C-6F.

Furthermore, different, advantageous embodiments are possible, as long as the law of reflection (angle of incidence=angle of reflection) is complied with for at least one definite angle α. FIGS. 6A-6F show certain possible embodiments with different angles β of the reflection element 11 relative to the transmission light 7 or different sections D.

Figure 6A:
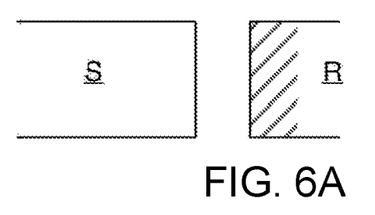
FIGS. 6A-6F show a sensor arrangement according to the present disclosure with sensor section and reflection section in different embodiments of both.
Figure 6B:
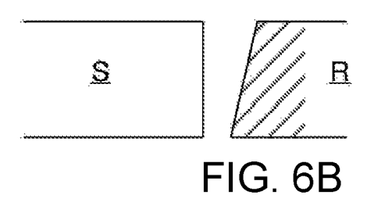
Figure 6C:
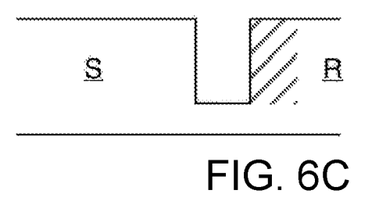
Figure 6D:
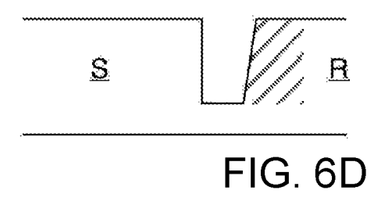
Figures 6E, 6F:
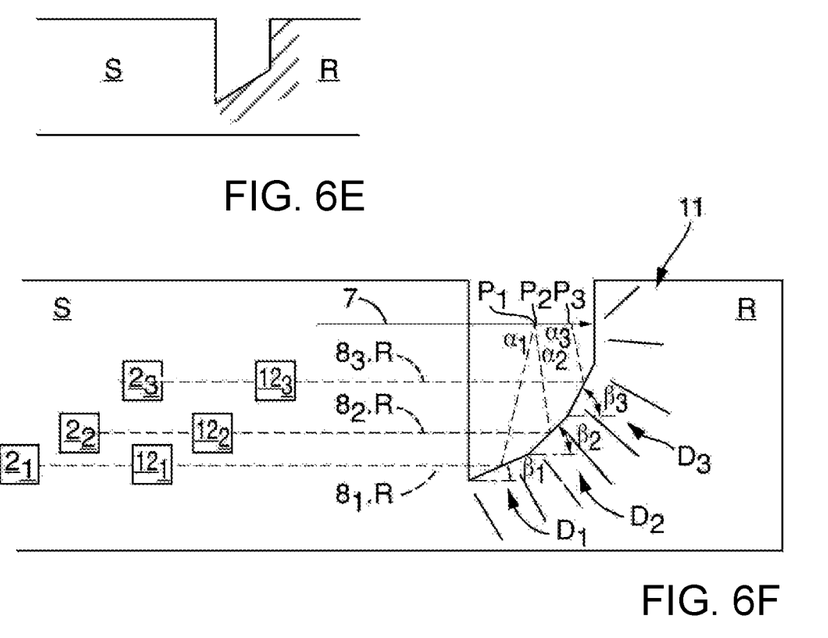
Figure 7:
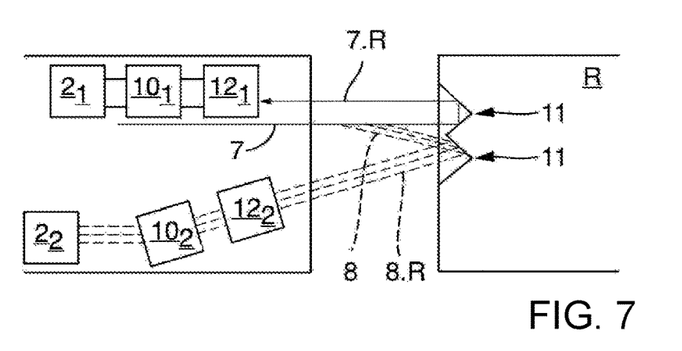
FIG. 7 shows the sensor arrangement according to the present disclosure in another embodiment with respect to the reflection element.

FIG. 6F, which shows four sections $D_1$, $D_2$, $D_3$, $D_4$ of the reflection element 11, will be explained briefly. By using several sections with respectively different arrangements with respect to the transmission light 7, and thus with different angles $β_1$, $β_2$, $β_3$, different measurement angles $α_1$, $α_2$, $α_3$ can be realized in a relatively space-saving manner. Despite the different measurement angles $α_1$, $α_1$, $α_3$, the reception light $8_1.R$, $8_2.R$, $8_3.R$ is back reflected parallel to the transmission light 7, due to the different sections $D_1$, $D_2$, $D_3$ with the arrangement with the angles $β_1$, $β_2$, $β_3$. The respectively associated solid angle filters $12_1$, $12_2$, $12_3$ and receivers $2_1$, $2_2$, $2_3$ are arranged along the longitudinal direction, and, for example, offset. In this way, the sensor arrangement 20 is indeed longer but not wider. This further results in a more flexible and simpler construction.

In another embodiment, the reflection element 11 is implemented as a prism, for example, a reflection prism or the like. In this regard, see FIG. 7.

As mentioned, the sensor arrangement 20 respectively comprises an optical window 6 in the boundary area between the sensor section S and the measuring chamber 5, as well as between the measuring chamber 5 and the reflection section R. For example, the optical window 6 toward the medium 3 can be designed according to different, advantageous possibilities: a window 6 for incoming transmission light 7 and all reflected reception light 8 (see FIG. 8A). Or, a common window 6a for incoming and directly-reflected transmission light 7, 7.R and another window 6b for reflected reception light 8 (see FIG. 8B). Or, for each reception light $8_1.R$, $8_2.R$ that was scattered at different measurement angles $α_1$, $α_2$, its own window $6_1$, $6_2$ (see FIG. 8C).

Generally, the window 6 is made of, for example, sapphire glass, quartz glass, or the like. The window 6 and the housing of the sensor arrangement 20 are rigidly connected to one another. For example, the window 6 and the housing are connected to one another in a medium-tight manner. The window 6 and the housing are, for example, connected to one another by gluing, soldering, etc.

The invention claimed is:

1. A sensor arrangement for determining a turbidity of a liquid medium, comprising:
a sensor section including at least one light source for sending transmission light into a measuring chamber, and at least one receiver associated with the light source for receiving reception light from the measuring chamber, wherein the transmission light is converted into the reception light in the measuring chamber by the medium due to scattering at a measurement angle, and the reception light received by the receiver is a measure of the turbidity of the medium,
wherein a reflection element is arranged in contact with the medium such that the reception light is reflected at the reflection element as first measurement light and second measurement light, wherein the first measurement light includes a portion of the transmission light that is first scattered at the measurement angle and then reflected at the reflection element, and wherein the second measurement light includes a portion of the transmission light that is first reflected at the reflection element and then scattered at the measurement angle.

2. The sensor arrangement of claim 1, wherein the sensor section further includes at least one solid angle filter that directs the light scattered by the medium and reflected by the reflection element onto the receiver, and wherein only light scattered at the measurement angle passes through the solid angle filter.

3. The sensor arrangement of claim 2, wherein the solid angle filter includes at least one optical beam-shaping component.

4. The sensor arrangement of claim 2, wherein the solid angle filter comprises a hollow cylinder having an inner diameter and a length, the hollow cylinder structured to absorb at least a portion of the reception light and, due to the inner diameter and the length, to allow only the portion of the reception light that was scattered at the measurement angle to pass therethrough.

5. The sensor arrangement of claim 2, wherein the solid angle filter comprises a block including a number of openings, each opening having an opening diameter and each opening being spaced from adjacent openings by a distance, the block structured to absorb at least a portion of the reception light and, due to the number of openings, the opening diameter of the openings and the distance of the openings from one another, to allow only the portion of the reception light that was scattered at the measurement angle to pass therethrough.

6. The sensor arrangement of claim 1, wherein the sensor section includes the reflection element.

7. The sensor arrangement of claim 1, wherein transmission light is scattered at a first measurement angle and at least one second measurement angle, and the sensor arrangement further comprises a first solid angle filter for the first measurement angle and at least one second solid angle filter for the second measurement angle.

8. The sensor arrangement of claim 7, the sensor arrangement comprising a first receiver for reception light scattered at the first measurement angle and a second receiver for reception light scattered at the second measurement angle.

9. The sensor arrangement of claim 7, the sensor arrangement comprising a first light source disposed to emit transmission light into the measuring chamber at a first angle of incidence and a second light source disposed to emit transmission light into the measuring chamber at a second angle of incidence, wherein transmission light of the first light source is scattered at a first measurement angle and the transmission light of the second light source is scattered at the second measurement angle.

10. The sensor arrangement of claim 7, wherein the reflection element includes a first section and at least one second section, and wherein the first section reflects light at a first angle of reflection, and the second section back reflects light at a second angle of reflection in the direction of the first or second solid angle filters, respectively.

11. The sensor arrangement of claim 1, wherein the reflection element is disposed at an angle of other than 90° to the transmission light.

12. The sensor arrangement of claim 1, the sensor arrangement further comprising a first window and at least a second window, wherein the first window is disposed at or between the sensor section and the measuring chamber and is transparent to the transmission light, and wherein the at least second window is disposed at or between the measuring chamber and the sensor section and is transparent to the reception light.

13. The sensor arrangement of claim 12, wherein the first window and the second window are configured as a common window.

14. The sensor arrangement of claim 12, the sensor arrangement further comprising one window per measurement angle, wherein the respectively scattered reception light passes through the corresponding window.

15. A sensor arrangement for determining a turbidity of a liquid medium, comprising:
   a sensor section including at least one light source for sending transmission light into a measuring chamber, and at least one receiver associated with the light source for receiving reception light from the measuring chamber, wherein the transmission light is converted into the reception light in the measuring chamber by the medium due to scattering at a measurement angle, and the reception light received by the receiver is a measure of the turbidity of the medium,
   wherein the reception light is reflected at a reflection element, the reflection element in contact with the medium; and
   a solid angle filter arranged such that the light scattered by the medium and reflected by the reflection element is directed onto the receiver, wherein only light scattered at the measurement angle passes through the solid angle filter, and
   wherein the solid angle filter comprises a hollow cylinder having an inner diameter and a length, hollow cylinder structured to absorb at least a portion of the reception light and, due to the inner diameter and the length, to allow only the portion of the reception light that was scattered at the measurement angle to pass therethrough.

16. The sensor arrangement of claim 15, wherein the sensor section includes the reflection element.

17. A sensor arrangement for determining a turbidity of a liquid medium, comprising:
   a sensor section including at least one light source for sending transmission light into a measuring chamber, and at least one receiver associated with the light source for receiving reception light from the measuring chamber, wherein the transmission light is converted into the reception light in the measuring chamber by the medium due to scattering at a measurement angle, and the reception light received by the receiver is a measure of the turbidity of the medium,
   wherein the reception light is reflected at a reflection element, the reflection element in contact with the medium; and
   a solid angle filter arranged such that the light scattered by the medium and reflected by the reflection element is directed onto the receiver, wherein only light scattered at the measurement angle passes through the solid angle filter, and
   wherein the solid angle filter comprises a block including a number of openings, each opening having an opening diameter and each opening being spaced from adjacent openings by a distance, the block structured to absorb at least a portion of the reception light and, due to the number of openings, the opening diameter of the openings and the distance of the openings from one another, to allow only the portion of the reception light that was scattered at the measurement angle to pass therethrough.

18. The sensor arrangement of claim 17, wherein the sensor section includes the reflection element.

* * * * *

UNITED STATES PATENT AND TRADEMARK OFFICE
CERTIFICATE OF CORRECTION

PATENT NO.         : 10,094,775 B2
APPLICATION NO.    : 15/372491
DATED              : October 9, 2018
INVENTOR(S)        : Thilo Krätschmer et al.

It is certified that error appears in the above-identified patent and that said Letters Patent is hereby corrected as shown below:

In the Claims

Claim 10 at Column 10, Lines 57-58:
Delete "back" after the word "section" and before the word "reflects".

Signed and Sealed this
Eighth Day of January, 2019

Andrei Iancu
*Director of the United States Patent and Trademark Office*